United States Patent
Monnier et al.

(10) Patent No.: US 6,172,245 B1
(45) Date of Patent: Jan. 9, 2001

(54) GAS PHASE PROCESS FOR THE EPOXIDATION OF NON-ALLYLIC OLEFINS

(75) Inventors: John Robert Monnier, Kingsport, TN (US); Jerome Leonard Stavinoha, Jr., Longview, TX (US); Gary Wayne Hartley, Kingsport, TN (US); Emily Elizabeth Jameson, Kingsport, TN (US); Scott Donald Barnicki, Kingsport, TN (US)

(73) Assignee: Eastman Chemical Company, Kingsport, TN (US)

( * ) Notice: Under 35 U.S.C. 154(b), the term of this patent shall be extended for 0 days.

(21) Appl. No.: 09/465,100

(22) Filed: Dec. 16, 1999

(51) Int. Cl.⁷ .................................................. C07D 301/10
(52) U.S. Cl. ............................................. 549/534; 549/536
(58) Field of Search ....................... 549/534, 536

(56) References Cited

U.S. PATENT DOCUMENTS

| | | |
|---|---|---|
| 4,039,561 | 8/1977 | Mitsuhata et al. . |
| 4,169,099 | 9/1979 | Khoobiar . |
| 4,267,073 | 5/1981 | Nielsen et al. . |
| 4,356,312 | 10/1982 | Nielsen et al. . |
| 4,389,338 | 6/1983 | Mitsuhata et al. . |
| 4,769,358 | 9/1988 | Kishimoto et al. . |
| 4,833,261 | 5/1989 | Lauritzen . |
| 4,897,498 | 1/1990 | Monnier et al. . |
| 4,916,243 | 4/1990 | Bhasin et al. . |
| 4,950,773 | 8/1990 | Monnier et al. . |
| 5,081,096 | 1/1992 | Monnier et al. . |
| 5,102,848 | 4/1992 | Soo et al. . |
| 5,117,012 | 5/1992 | Stavinoha, Jr. et al. . |
| 5,138,077 | 8/1992 | Monnier et al. . |
| 5,145,824 | 9/1992 | Buffum et al. . |
| 5,145,968 | 9/1992 | Monnier et al. . |
| 5,312,931 | 5/1994 | Stavinoha, Jr. . |
| 5,362,890 | 11/1994 | Stavinoha, Jr. et al. . |
| 5,618,954 | 4/1997 | Boeck et al. . |
| 5,756,779 | 5/1998 | Stavinoha, Jr. . |
| 5,905,161 | 5/1999 | Boeck et al. . |
| 5,945,550 | 8/1999 | Barnicki et al. . |

OTHER PUBLICATIONS

Brunauer, S. et al., J. Am. Chem. Soc. 60,309–16 (1938).
Inui, T. et al., Retardative Effect of Amine on Ethylene Oxidation over Silver, Journal of Catalysis, 375–384, vol. 52 (1978).
Van Santen, R.A. et al., The Mechanism of Ethylene Epoxidation, Advances in Catalysis, 265–321, vol. 35 (1987).

Primary Examiner—Ba K. Trinh
(74) Attorney, Agent, or Firm—Matthew W. Smith; Harry J. Gwinnelll

(57) ABSTRACT

Disclosed herein is an improved gas phase process for the selective epoxidation of non-allylic olefins wherein the epoxidation is carried out in the presence of one or more volatile, nitrogen-containing, basic compounds. The presence of a nitrogen-containing basic compound in the olefin-containing reaction gas or vapor suppresses the formation of an organic resinous material which coats the catalyst, thereby decreasing catalyst activity and life and also increases substantially the activity of the epoxidation catalyst. The disclosed process is particularly useful for the continuous manufacture of 3,4-epoxy-1-butene from 1,3-butadiene.

14 Claims, No Drawings

GAS PHASE PROCESS FOR THE EPOXIDATION OF NON-ALLYLIC OLEFINS

INTRODUCTION

This invention pertains to an improved gas phase process for the selective epoxidation of non-allylic olefins wherein the epoxidation is carried out in the presence of one or more volatile, nitrogen-containing, basic compounds. The presence of a nitrogen-containing basic compound in the olefin-containing reaction gas or vapor suppresses the formation of an organic resinous material which coats the catalyst, thereby decreasing catalyst activity. This resinous material (foulant) also can coat and foul process equipment, thereby impeding or obstructing gas flow through the reactor and associated equipment. The inclusion of a nitrogen-containing basic compound in the olefin-containing reaction gas also has been found to increase substantially the activity of the epoxidation catalyst.

BACKGROUND OF THE INVENTION

Processes for the selective epoxidation of olefins which contain no allylic hydrogen atoms (non-allylic olefins) or olefins which contain hindered allylic hydrogen atoms are described by Monnier and Muehlbauer in U.S. Pat. Nos. 4,897,498, 4,950,773, 5,081,096, 5,138,077 and 5,145,968. Stavinoha and Tolleson disclose in U.S. Pat. No. 5,117,012 the selective epoxidation of 1,3-butadiene (butadiene) to 3,4-epoxy-1-butene (EpB) by contacting a mixture comprising 1,3-butadiene, oxygen and methane with a supported silver catalyst at elevated temperatures. Stavinoha, Monnier, Hitch, Nolen and Oltean describe in U.S. Pat. No. 5,362,890 the advantages resulting from the use of a $C_2$–$C_6$ paraffin hydrocarbon as an inert diluent in the feed gas in the epoxidation of certain olefins such as 1,3-butadiene.

The epoxidation of olefins such as butadiene in the presence of a modified, supported, silver catalyst to an epoxide such as 3,4-epoxy-1-butene according to known processes such as those described in the above referenced patents results in the co-production of a high-boiling, organic, resinous material. Generally, the rate of formation of the foulant material is dependent, at least in part, upon pressure within the epoxidation reactor with increased pressures resulting in increased rates of foulant formation. This foulant material coats the catalyst and thereby decreases catalyst activity which, in turn, results in lower conversion of the olefin reactant and production of the desired epoxide. This foulant also may coat and foul process equipment, thereby impeding or obstructing gas flow through the reactor and associated equipment. Build-up of the foulant material over extended periods of operation of the continuous epoxidation process significantly shortens the length of service of catalyst, results in an unacceptable pressure drop through the reactor during normal operation, lowers catalytic activity, and ultimately results in complete blockage of gas flow through the reactor. Removal of catalyst material coated or covered with the organic foulant from the reactor tubes typically used in the epoxidation of olefins is extremely difficult, requiring considerable time to remove the foulant from the reactor tubes and associated equipment downstream from the tubular reactor.

U.S. Pat. Nos. 5,618,954 and 5,905,161 are directed to reducing foulant formation during the epoxidation of butadiene. These patents disclose the use of 5–80% water in the feed gas to the epoxidation reactor to lower the rate of foulant formation. However, even with the water addition, fouling occurs and the supported silver catalyst requires frequent regeneration in a gas stream containing oxygen and water vapor. Furthermore, the addition of water to a process gas stream containing reactive epoxides can result in the formation of the corresponding diols, e.g., 3-butene-1,2-diol and 2-butene-1,4-diol, which are reactive species that can further react to form organic foulant residue. Although it is not known exactly how the organic foulant forms, it has been experimentally determined that 3,4-epoxy-1-butene, oxygen, and water are required for growth, or propagation of the organic foulant. Therefore, addition of water to suppress the formation of organic foulant is actually detrimental to the goal of lowering the rate of organic foulant formation. Finally, addition of high concentrations of water vapor described in the cited patents can result in the degradation of the modified silver catalysts that are employed to catalyze the formation of the olefin epoxides.

Inui and Tanabe, *Journal of Catalysis*, 52, 375–384(1978) discuss the effects of the addition of various levels of ammonia and substituted amines, such as monomethylamine, dimethylamine, trimethylamine, ethylamine, diethylamine, and ethanolamine, etc. to the reactor feedstream during ethylene epoxidation. The authors report that the addition of ammonia and such amines in the range of 200–34000 ppmv to the reactor feedstream resulted in decreases in the rate of ethylene oxide formation. At the higher levels, catalytic activity was completely suppressed.

BRIEF SUMMARY OF THE INVENTION

We have discovered that the rate of formation of resinous, high boiling, organic foulant during the epoxidation of olefins can be significantly reduced, and possibly eliminated, by including at least one nitrogen-containing basic compound in the gaseous reaction mixture. Our invention, in its broader aspects, provides a process for the preparation of the monoepoxide of an olefin reactant selected from norbornene, norbornadiene and olefins having the general formula

wherein $R^1$ is hydrogen or alkyl and $R^2$ is an aryl radical or the group

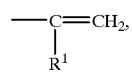

provided that the olefins of formula (I) contain more than 2 carbon atoms and do not contain any allylic hydrogen atoms, which comprises contacting a reaction gas comprising said olefin reactant, oxygen, an inert diluent, and at least 5 parts per million by volume (ppmv) of at least one nitrogen-containing basic compound with a supported silver epoxidation catalyst at a temperature of about 175 to 230° C.; and recovering a gas containing said monoepoxide of the olefin reactant.

A more specific embodiment of the present invention is a continuous process for the preparation of the monoepoxide of an olefin reactant selected from norbornene, norbornadiene and olefins having the general formula

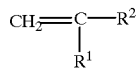

wherein $R^1$ is hydrogen or alkyl and $R^2$ is an aryl radical or the group

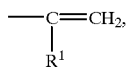

provided that the olefins of formula (I) contain more than 2 carbon atoms and do not contain any allylic hydrogen atoms, which comprises the steps of:

(1) continuously feeding a gas comprising about 3 to 30 mole percent of said olefin reactant, about 3 to 30 mole percent oxygen, about 40 to 90 mole percent of an inert diluent, and at least 5 parts per million by volume (ppmv) of at least one nitrogen-containing basic compound to an epoxidation zone containing a supported silver epoxidation catalyst and maintained at a temperature of about 175 to 230° C.; and (2) continuously removing from the epoxidation zone a gas comprising about 0.5 to 5.0 mole percent of said monoepoxide of the olefin reactant, about 2 to 28 mole percent of said olefin reactant, about 2 to 28 mole percent oxygen and about 40 to 90 mole percent of the inert diluent.

The inclusion of the nitrogen-containing basic compound in the epoxidation zone or reactor suppresses foulant formation to a degree which permits operation of the epoxidation reactor at higher pressures which results in a higher rate of conversion of the olefin reactant and, thus, a higher rate of production of the monoepoxide. The nitrogen-containing basic compound in the epoxidation zone also results in an increase in the activity, e.g., an increase in activity of 10 to 30%, of the supported silver epoxidation catalyst. Another advantage provided by the present invention is that the nitrogen-containing basic compound fed to the epoxidation zone can provide the basic compound employed in the product recovery process described in U.S. Pat. No. 5,756,779 to reduce formation of butenediols.

DETAILED DESCRIPTION

The nitrogen-containing basic compounds which may be used in the present invention comprises ammonia and amines which exist in the gaseous state and are substantially inert (nonreactive) with respect to the olefin reactant, the monoepoxide product and oxygen under the conditions of temperature and pressure within the epoxidation zone. Example of the amines which may be used include mono-, di- and tri-alkyl amines such monomethylamine, dimethylamine, trimethylamine, diethylamine, triethylamine, monopropylamine, dipropylamine, tripropylamine, monobutylamine, dibutylamine, tributylamine, higher homologous mono-, di-, and tri-alkylamines and mixed mono-, di-, and tri-alkylamines. Diamines, such as ethylenediamine and the like as well as triamines, such as ethylenetriamine and the like are included within the scope of the present invention. Cyclic amines such as pyrrolidine, piperidine, morpholine, piperazine, pyrrole, pyridine, and the lutidines also are contemplated within the scope of the invention. Mono-, di-, and tri-substituted amines may be used in the process of the present invention to reduce formation of resinous, organic foulant. However, when the primary goal is increased catalytic activity, the nitrogen-containing basic compound should be selected from ammonia and amines which contain at least one N—H bond, thus limiting the amines to mono- and di-substituted amines including diamines, such as ethylenediamine, and cyclic amines. The amine preferably has a boiling point of less than about 150° C. and most preferably is a mono- or di-alkylamine containing up to about 12 carbon atoms.

The amount of ammonia and/or amine used in the epoxidation process is at least 5 ppmv based on the total volume of materials fed to the epoxidation zone. Normally, the amount of ammonia and/or amine fed will not exceed 2000 ppmv. The preferred range of ammonia and/or amine fed to the epoxidation zone is in the range of about 20 to 500 ppmv based on the total volume of the gaseous materials fed to the epoxidation zone. Ammonia and volatile, low molecular weight mono- and di-substituted amines constitute the preferred nitrogen-containing basic compound which preferably are used in concentrations of about 20 to 500 ppmv based on the total volume of the gaseous materials fed to the epoxidation zone. The ammonia and/or amine may be added to the epoxidation reaction zone in a variety of ways. For example, it can be mixed with the olefin to be oxidized and/or the oxygen-containing gas prior to contacting with the catalyst, or the ammonia and/or amine can be introduced to the reaction zone separately from the feed olefin and/or the oxygen-containing gas. The ammonia and/or amine may be added continuously or discontinuously to the epoxidation reaction zone. For example, the ammonia/amine may be fed for a period of time which is sufficient to produce an increase in catalyst activity and process productivity as determined from increases in the conversion of olefin reactant relative to the conversion of olefin prior to addition of ammonia and/or amine to the feedstream. The ammonia and/or amine feed then may be discontinued while the increase in catalyst activity continues for prolonged periods of time.

The supported silver epoxidation catalysts which may be used in the process provided by our invention are known materials which may be prepared according to published procedures including the catalyst manufacturing procedures described in U.S. Pat. Nos. 4,039,561, 4,169,009, 4,267,073, 4,389,338, 4,769,358 and 5,081,096. Thus, the catalysts useful in the present process comprise a catalyst support material having deposited on its surface about 1 to 30 weight percent silver and about 10 to 5000 parts per million by weight (ppmw) of an epoxidation catalyst modifier selected from alkali earth metals, alkaline earth metals and thallium. The weight percentage silver and ppmw modifier (also referred to as promoter) are based on the total weight of the catalyst, i.e., the finished catalyst. Although the modifier component of the catalyst may exist as a salt, oxide or hydroxide of the modifier element, the modifier concentration of the catalyst is based on modifier element alone.

The support component of the catalysts may be selected from the large number of conventional, porous, refractory catalyst carriers or support materials which are essentially inert in the presence of the ethylenically unsaturated compound and oxygen-containing gas feeds and the products in the processes in which the catalysts are employed. Such conventional materials may be of natural or synthetic origin and preferably are of a macroporous structure, that is, a structure having a surface area below about 10 m²/g. These support materials typically have an apparent porosity of greater than 20%. Supports having a siliceous and/or aluminous composition are, in general, preferred. Specific examples of suitable supports are the aluminum oxides (including the materials sold under the trade name "Alundum"), pumice, magnesia, zirconia, kieselguhr, fuller's earth, silicon carbide, porous agglomerates comprising silicon and/or silicon carbide, silica, selected clays, artificial and natural zeolites and ceramics. Refractory supports particularly useful in the preparation of the catalysts useful in the process of our invention comprise the aluminous materials, in particular those containing alpha alumina. In the case of alpha alumina-containing supports, preference is given to those having a specific surface area as measured by the B.E.T. method of from about 0.03 to 10 $m^2/g$ and an apparent porosity as measured by conventional mercury or water absorption techniques of from about 25 to about 60% by volume. The B.E.T. method for determining specific surface area is described in detail in Brunauer, S., Emmett, P. H., and Teller, E., J. Am. Chem. Soc., 60, 309–16 (1938).

The following materials are specific examples of the catalyst supports which may be used.

I. Norton SN-06595, a fluidizable powder having a surface area of 0.26 $m^2/g$, a total pore volume of 0.675 cc (Hg)/gm, median pore diameter 19 microns ($\mu$), a packing density of 0.98 $g/cm^3$, and a chemical composition (weight percent) of: $Al_2O_3$—84.7, $SiO_2$—13.4, $Fe_2O_3$—0.21, $TiO_2$—0.47, CaO—0.21, MgO—0.12, $Na_2O$—0.15, $K_2O$—0.26).

II. Norton SN-08228, 0.1875 inch pellets with a surface area of 0.26 $m^2/g$, a total pore volume of 0.23 cc(Hg)/gm, median pore diameter of 19$\mu$, a packing density of 0.90 $g/cm^3$, and a chemical composition (weight percent) of: alumina —84.7, $SiO_2$—13.4, $Fe_2O_3$—0.21, $TiO_2$—0.47, CaO—0.21, MgO—0.12, $Na_2O$—0.15, $K_2O$—0.26.

III. Norton SA-5252, 0.1875 inch spheres with a surface area of 0.39 $m^2/g$, a total pore volume of 0.36 cc(Hg)/gm, median pore diameter of 5.4$\mu$, a packing density of 0.94 $g/cm^3$ and a chemical composition (weight percent) as follows: $Al_2O_3$—93.1, $SiO_2$—5.6, $Fe_2O_3$—0.3, $TiO_2$—0.1, CaO—0.1, MgO—0.3, $Na_2O$—0.1, $K_2O$—0.1.

IV. Norton 5552 Alumina Rings—0.25 inch rings having a surface area of 0.43 $m^2/g$, a total pore volume of 0.37 cc (Hg)/gm, a median pore diameter of 7$\mu$, a packing density of 0.80 $g/cm^3$, and a chemical composition (weight percent) of: $Al_2O_3$—93.1, $SiO_2$—5.6, $Fe_2O_3$—0.3, $TiO_2$—0.1, CaO—0.1, MgO—0.3, $Na_2O$—0.1, $K_2O$—0.1.

V. Norton SN-82501, 0.1875 inch spheres having a surface area of 0.13 $m^2/g$, a total pore volume of 0.37 cc(Hg)/gm, a median pore diameter of 32.5$\mu$, a packing density of 0.88 $g/cm^3$, and a chemical composition (weight percent) of: $Al_2O_3$—85.0, $SiO_2$—12.0, and the remaining 3% as $Fe_2O_3$, $TiO_2$, CaO, MgO, $Na_2O$ and $K_2O$.

Although not preferred, other support materials which may be used include zinc oxide, e.g., having a surface area of about 3.9 $m^2/g$ and a particle size of about 75–250$\mu$; titania, e.g., having a surface area of about 0.5 $m^2/g$ and a particle size of about 40–75$\mu$; calcium oxide; silica, e.g., having a surface area of about 0.18 $m^2/g$ and a particle size of about 75–250$\mu$; barium oxide, e.g., having a surface area of about 1 $m^2/g$ and a particle size of 40–75$\mu$; boron nitride; silicon nitride; and silicon carbide.

A preferred class of support materials comprise low surface area, fused, alpha alumina supports which have relatively uniform pore diameters and are more fully characterized by having (1) B.E.T. specific surface areas of from about 0.1 $m^2/g$ to about 2.0 $m^2/g$, preferably about 0.3 $m^2/g$ to about 1.0 $m^2/g$, and (2) apparent porosities of from about 42% to about 60%, preferably from about 46% to about 58%.

The actual physical form of the catalyst support is not particularly important. While the form of the catalyst support has little effect on catalyst activity, practical considerations such as ease of heat transfer, mass transfer, pressure drop due to fluid flow restrictions, efficiency of gas-liquid—solid contacting, catalyst durability, and the like make the use of defined shapes such as spheres, pellets, extrudates, rings, saddles, and the like preferred. Conventional commercial fixed-bed reactors used in the epoxidation of ethylenically-unsaturated compounds typically are in the form of a plurality of parallel, or series of, elongated tubes (in a suitable shell). In such reactors, it is desirable to employ a support formed into a rounded shape, such as, for example, spheres, pellets, rings, tablets, and the like, having diameters of from about 0.1 inch to about 0.8 inch.

A preferred method of preparing the catalysts from an inorganic silver compound comprises the steps of (1) forming a catalyst precursor by contacting, in either one or two steps, a porous support material with aqueous solutions of an inorganic silver compound and a modifier compound and drying the resulting impregnated support material, (2) optionally calcining the catalyst precursor wherein a gas such as air, oxygen-depleted air, nitrogen, argon, helium or the like is passed over or through the catalyst precursor at elevated temperatures, and (3) intimately contacting at a temperature of about 170 to 600° C. the catalyst precursor with a gas comprising (i) hydrogen or (ii) an inert gas containing at least 4 volume percent hydrogen. The preparation of the catalysts from an organic silver compound such as a silver amine oxalate, e.g., silver bis-ethylenediamine oxalate, comprises the steps of (1) forming a catalyst precursor by contacting, in either one or two steps, a porous support material with aqueous solutions of an organic silver compound and a modifier compound and drying the resulting impregnated support material, (2) optionally calcining the catalyst precursor wherein a gas such as air, oxygen-depleted air, nitrogen, argon, helium or the like is passed over or through the catalyst precursor at elevated temperatures, and (3) heating the catalyst precursor at a temperature of about 150 to 300° C. to thermally decompose the organic silver compound.

The catalyst precursors may be prepared employing techniques well known to those of skill in the art, such as, for example, by precipitation of suitable silver and modifier compounds on the support, by impregnation, by coprecipitation of the silver and modifier compounds and the support material, by grinding together the support material and the silver and modifier compounds in particulate form and the like. The order in which the modifier is incorporated onto the support material is not critical, e.g., the support may be contacted with a silver source, then the modifier, or the support may be contacted with the modifier compound, then a silver compound, or the support material may be contacted simultaneously with both a modifier compound and a silver compound.

The silver compound employed in the preparation of the catalyst precursor is not critical. Typically, the preparation of the catalyst precursor comprises impregnating the support material with a solution of a silver compound in water, an alcohol, a glycol ether, or a mixture thereof. Exemplary compounds are silver nitrate, silver oxalate, silver acetate, and the like. Those skilled in the art recognize that certain organic silver compounds require the addition of ammonia or an amine in order to solubilize the organic silver compound in an aqueous medium; thus, the use of such solvation-promoting additives is contemplated in the practice of the present invention.

The catalysts may contain about 1 to 30 weight percent silver, calculated as elemental or metallic silver and based on the total weight of active catalyst. The loading level of silver on the support preferably is within the range of about 2 up to 25 weight percent, most preferably about 5 to 20 weight percent, elemental silver. The silver typically is present in the form of uniformly-spaced, discontinuous, adherent, substantially hemispherical, discrete particles having an essentially uniform diameter of about 0.1 to 5.0μ. Catalysts bearing silver particles less than about 0.1μ give inferior catalytic results whereas silver particles larger than about 5.0μ do not appear as uniformly-spaced, discontinuous particles but appear to give a continuous layer of inter-grown crystals which results in a catalyst having inferior activity due to loss of silver surface area.

The chemical form of the modifier component of the finished catalysts is not known. However, the heat and/or hydrogen treatment given to the impregnated support in the reduction of the silver salts to metallic silver most likely converts the modifier compounds or salts to an oxide, oxidic or halide compound. The amount of modifier compound present on the catalyst support is expressed herein as the weight percent, based on the total weight of the catalyst, of the modifier element rather than the modifier compound.

The amount of modifier element present on the catalyst surface may vary substantially depending, for example, on the particular support material employed and/or the surface area thereof and the amount of silver on the catalyst. Generally, the amount of modifier element on the active catalyst is in the range of about 10 to 5000 parts per million (ppm, by weight) based on the total weight of the active catalyst. The concentration of modifier preferably is in the range of about 20 to 3000 ppm with amounts in the range of about 50 to 1600 ppm (same basis) being especially preferred. The modifier element preferably is cesium, rubidium or thallium. Normally, the silver:modifier weight ratio of the finished or active catalysts is in the range of about 50:1 to 4000:1, preferably in the range of about 100:1 to 2500:1, and most preferably in the range of about 100:1 to 2000:1.

Silver and the modifier normally are the only active constituents which are added to the support materials in catalytically effective amounts. However, it is not unusual for substantial amounts, often up to about 10,000 ppm by weight of an alkali metal (usually potassium) to be present within the porous support due to (1) the use of support materials containing naturally occurring alkali metals or (2) the addition of alkali metal during support manufacture. These amounts of alkali metal present in the support in non-leachable form, rather than on the surface, do not appear to contribute to the performance of the catalysts.

The catalyst precursor comprising a catalyst support material having the silver and modifier compounds deposited thereon as described hereinabove is converted to an active catalyst by intimately contacting the precursor, after the optional calcination step, with a gas comprising (i) hydrogen, or (ii) an inert gas containing at least about 4 volume percent hydrogen at a temperature of about 170 to 600° C. whereby the silver compound is reduced to elemental silver and the thallium metal compound is believed to be converted to an oxide and/or hydroxide. The particular conditions employed in the high temperature hydrogen treatment can vary substantially since the hydrogen concentration and temperature as well as contact times are interdependent. Alternatively, when the catalyst precursor comprises an organic silver compound, such as an aminesolubilized silver oxalate, the catalyst precursor may be converted to the active state by thermal decomposition in air at temperatures of about 150 to 300° C. Such thermal decomposition requires that the catalyst precursor be heated at a temperature and for a period of time sufficient to completely reduce the organic silver salt to metallic silver.

The olefin reactants which may be used in the process include norbornene, norbornadiene and olefins having the general formula

(I)

wherein $R^1$ is hydrogen or alkyl and $R^2$ is an aryl group, a tertiary alkyl group such as tertiary butyl, tertiary amyl, or tertiary octyl, or the group having the formula

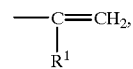

with the proviso that $R^1$ contains no hydrogen atoms in a position allylic to the ethylenic unsaturation, i.e., the >C==C< group or groups. The alkyl groups represented by $R^1$ may be unsubstituted or substituted alkyl having up to about 12 carbon atoms. Such alkyl groups preferably are unsubstituted alkyl of up to about 4 carbon atoms. When the reactant is an olefin having the formula

(I)

the $R^1$ substituents may be the same or different. The aryl groups represented by $R^2$ may be unsubstituted or substituted carbocyclic aryl having 6 to 10 carbon atoms, e.g., unsubstituted and substituted phenyl and naphthyl radicals. Examples of the substituents which may be present on the aryl groups include alkyl of up to about 4 carbon atoms, alkoxy of up to about 4 carbon atoms, halogen such as chloro and bromo, hydroxy, vinyl, and the like.

The epoxides produced from the olefins of formula (I) in accordance with the epoxidation process described herein have the general formula

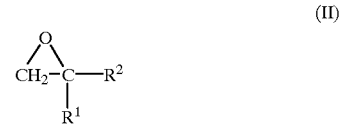
(II)

wherein $R^1$ and $R^2$ are defined above. The process provided by our invention is especially useful for the selective monoepoxidation of butadiene to 3,4-epoxy-1-butene.

Our novel process may be carried out at a temperature in the range of about 175 to 230° C. with the range of 185 to 225° C. being particularly preferred. The pressure within the epoxidation zone may range from about 0.5 to 20 bar absolute (bara), preferably about 1 to 10 bara. It is apparent that the particular combination of temperature and pressure is selected so as to maintain all of the components of the feed to the epoxidation zone in the gaseous state. As mentioned above, one of the advantages provided by the present invention is that the epoxidation process may be operated on a commercial scale at pressures higher than those which have been utilized previously.

The inert diluent which may be used in the present process may be selected from helium, nitrogen, and paraffin hydrocarbons such as straight- or branched-chain alkanes containing up to about 6 carbon atoms, e.g., methane, ethane, propane, butane, isobutane, pentane and hexane.

The advantages and benefits provided by the present invention may be achieved by feeding to the epoxidation zone a gas comprising about 3 to 30 mole percent of said olefin reactant, about 3 to 30 mole percent oxygen and about 40 to 90 mole percent of a paraffin hydrocarbon containing 1 to 6 carbon atoms, wherein the oxygen:paraffin hydrocarbon mole ratio is in the range of about 0.03:1 to 0.75:1, and 2 to 2000 ppmv of ammonia and/or an amine, preferably about 20 to 500 ppmv ammonia. Normally, the feed gas also will contain a total of about 1 to 10 mole percent of other components such as water, carbon dioxide, argon and recycled epoxide product. Up to about 10 mole percent of the inert diluent component of the feed gas may be made up of one or more other inert gases such as such as argon, methane and nitrogen. The feed gas to our novel continuous process preferably comprises (1) about 5 to 25 mole percent of the olefin reactant, (2) about 5 to 25 mole percent oxygen, (3) about 40 to 80 mole percent of a paraffin hydrocarbon containing 1 to 6 carbon atoms, (4) 20 to 500 ppmv ammonia and/or amine, and (5) a total of about 0 to 10 mole percent of other components selected from water, carbon dioxide, argon and recycled epoxide product.

The selectivity of our novel epoxidation process may be increased by performing the process in the presence of halide, typically chloride, ion. Halide ion may be provided to the process by using a halide (chloride) salt of the modifier employed in the preparation of the catalysts. Alternatively, some or all of the halide ion may be provided to the process by including one or more organic halides in the gaseous feed, e.g., in a concentration of about 1 to 40 ppm. Examples of such organic halides include compounds having the formula $R^3X$ wherein $R^3$ is a hydrocarbyl group or a halogenated hydrocarbyl group containing up to about 8 carbon atoms and X is a halogen atom, preferably chloro or bromo, and wherein $R^3$ contains at least one hydrogen atom which is sufficiently acidic so as to render $R^3X$ capable of undergoing dehydrohalogenation under the reaction conditions. Exemplary organic halides include $C_1$ compounds such as methyl chloride, methyl bromide, methylene chloride, methylene bromide, chloroform and bromoform, and the like; $C_2$ compounds such as ethyl chloride, ethyl bromide, dichloroethane, dibromoethane, vinyl chloride, dichloroethylene, trichloroethylene, and the like; $C_3$ compounds such as dichloropropane, dibromopropane, dichloropropene, dibromopropene, and the like; $C_4$ compounds such as chlorobutane, bromobutane, dichlorobutane, dibromobutane, chlorobutene, bromobutene, dichlorobutene, dibromobutene, and the like; $C_5$ compounds such as mono-, di-, tri-, tetra-, and pentachloropentanes or pentenes, mono-, di-, tri-, tetra-, and pentabromopentanes or pentenes, cyclopentylchloride, cyclopentylbromide, and the like; $C_6$ compounds such as mono-, di-, tri-, tetra-, penta-, and hexachlorohexanes or hexenes, mono-, di-, tri-, tetra-, penta-, and hexabromohexanes or hexenes, cyclohexylchloride, cyclohexylbromide, chlorobenzene, bromobenzene, and the like; $C_7$ compounds such as chlorotoluene, bromotoluene, benzyl chloride, benzyl bromide, mono-, di-, tri-, tetra-, penta-, hexa-, and heptachloroheptanes or heptenes, mono-, di-, tri-, tetra-, penta-, hexa-, and heptabromoheptanes or heptenes, chlorocycloheptane, bromocycloheptane, and the like; $C_8$ compounds such as mono-, di-, tri-, tetra-, penta-, hexa-, hepta- and octachlorooctanes or octenes, mono-, di-, tri-, tetra-, penta-, hexa-, hepta-, and octabromooctanes or octenes, and the like; as well as mixtures of any two or more thereof.

The organic halide can be added to the oxidation reaction zone in a variety of ways. For example, it can be mixed with the olefin to be oxidized and/or the oxygen-containing gas prior to contacting with the catalyst, or the organic halide can be introduced to the reaction zone separately from the feed olefin and/or the oxygen-containing gas. The concentration of the organic halide in the feed to the epoxidation zone preferably is about 2 to 20 parts per million by volume (ppmv). Dichloroethane and chlorobutane are the preferred organic halides.

The addition of a nitrogen-containing basic material in the feed to the reactor also aids in decreasing the loss of EpB to butanediols in the recovery section of the process. The addition of a base to the recovery section of an EpB process is described in U.S. Pat. No. 5,756,779. Our invention thus further illustrates the methods of adding base to the recovery section. In fact, addition of ammonia and/or amine to the reactor feed provides excellent contact with the acidic components in the gaseous product stream, and thus reduces diol formation to a very low level and either reduces or eliminates the need to add an alkali metal base material to the recovery section.

EXAMPLES

The novel process of the present invention is further illustrated by the following examples. Unless stated otherwise, the epoxidation catalyst employed in the examples comprised a fused alumina support in the form of particles having diameters ranging from 0.7 to 1 cm having deposited thereon 12 weight percent silver and 1250 parts per million by weight (ppmw) cesium. These catalysts were prepared according to known procedures by impregnating the support material with solutions of a silver amine salt and cesium nitrate followed by a thermal decomposition/ reduction treatment in the presence of an oxygen-containing gas to convert the silver salt to silver metal.

Catalyst performance was measured after steady state operation had been reached for each combination of process conditions. Catalytic activity is expressed as mole percent of EpB (mole % EpB) in the reactor effluent where mole % EpB is defined as $$\frac{\text{Moles EpB in product effluent}}{\text{Total moles of all gas components in product effluent}} \times 100$$

and selectivity is the percent selectivity to epoxybutene is defined as $$\frac{\text{Moles butadiene converted to epoxybutene}}{\text{Moles butadiene converted to all products}} \times 100.$$

Catalytic activity also can be expressed as percent conversion of butadiene in the feed stream to all products:

$$\frac{\text{Moles butadiene converted to products}}{\text{Moles butadiene fed}} \times 100.$$

Comparative Example 1

Comparative Example 1 and Examples 1–3 were carried out in a reactor comprising a stainless steel, tubular reactor 45.7 cm (18 inches) long having an outside diameter of 9.5 mm (0.375 inches) and an inside diameter of 7.75 mm (0.305 inches). The reactor was jacketed with a brass collar 25.4 mm (1 inch) in diameter to maintain an approximate, isothermal catalyst temperature profile. An adjustable thermowell was inserted inside the catalyst bed. The catalyst (12.24 g) was loaded into the reactor and heated in flowing air in situ at 250° C. for 2 hours. The temperature was then lowered to 180° C. and the catalyst was "prechlorided" in a gas flow of 10 ppm 2-chlorobutane in n-butane for a period of 30 minutes. The thermowell confirmed a nearly isothermal bed profile over the 30.5 cm (12 inches) length of the catalyst bed. The epoxidation of butadiene then was commenced by feeding to the reactor/catalyst a gaseous feed stream composed of 9% (molar) butadiene and 18% (molar) oxygen with the balance being propane diluent containing 2–3 ppmv 2-chlorobutane at approximately 1 bara (15 pounds per square inch absolute—psia) total pressure. The reaction temperature was increased from 180 to 200° C. over a 20-hour period of time. Catalyst performance was monitored every two hours throughout the entire run by an in-line gas sampling loop that injected a gas sample into a Poraplot Q gas chromatographic column installed in an Hewlett-Packard 5890 Series Gas Chromatograph. The epoxidation process was operated at the described conditions for 20 hours and then was operated for an additional 190 hours at the following conditions of temperature (° C.) and total pressure (bara and psia):

| Hours of Operation | Temperature | Pressure |
|---|---|---|
| 21–40 | 200 | 4.14 60 |
| 41–70 | 205 | 7.24 105 |
| 71–140 | 205 | 4.14 60 |
| 141–210 | 210 | 7.24 105 |

The flow rate of the feed gas was adjusted for each combination of operating conditions to maintain a contact, or residence, time in the reactor of 1.6–1.7 seconds corresponding to a gas hourly space velocity (GHSV) of 2250 hr$^{-1}$. Following the completion of the evaluation after 210 hours of operation, the feed gas was replaced with flowing helium and the catalyst and reactor were cooled to room temperature. For the final 141–210 hours of operation, catalytic activity was 2.14% (mole) EpB at a selectivity of 84.3% to EpB, corresponding to a butadiene conversion of 28.3%.

The catalyst, which was substantially coated with organic foulant was carefully removed and then weighed. The catalyst plus foulant (plus very small amounts of inert preheat material, which were not able to be separated from the spent catalyst) was placed in a second tubular calcination tube, heated in flowing air at 500° C. for a period of 2 hours and then cooled. The catalyst was cooled to room temperature and then weighed. The catalyst, which weighed 13.328 g before calcination, weighed 12.610 g after calcination. Thus, the catalyst had gained 0.718 g of foulant during reaction, or the weight gain corresponded to 5.69% of the initial weight.

It is apparent that catalyst fouling of this magnitude will result in short catalyst lifetime at extended periods of operation.

Catalytic activity at steady-state reaction conditions for each of the combination of reaction conditions employed in Comparative Example 1 are summarized in Table I wherein Temp is reactor temperature in ° C. and Press is reactor pressure in bara. Conversion and selectivity are expressed in percent.

TABLE I

| Reaction Conditions | | Mole % EpB | Conversion | Selectivity |
|---|---|---|---|---|
| Temp | Press | Produced | of Butadiene | to EpB |
| 200 | 4.14 | 0.98 | 13.1 | 83.0 |
| 205 | 7.24 | 1.79 | 23.8 | 83.7 |
| 205 | 4.14 | 2.30 | 29.9 | 85.5 |
| 210 | 7.24 | 2.14 | 28.2 | 84.3 |

Example 1

Comparative Example 1 was repeated except that 50 ppmv ammonia was added to the gaseous feed stream after 20 hours of operation (when the reactor pressure was increased to 4.14 bara. The 50 ppm ammonia was maintained in the feed stream for the remainder of the butadiene epoxidation using the same the same reaction protocol detailed in Comparative Example 1. At the conclusion of the experiment, the catalyst was removed from the tubular reactor. The catalyst showed no visible signs of organic foulant and, when subjected to the calcination procedure described in Comparative Example 1, the percentage of organic foulant present on the catalyst was determined to be 0.40% of the catalyst removed from the reactor. Catalyst performance at each reaction condition of temperature and pressure is summarized in Table II below.

TABLE II

| Reaction Conditions | | Mole % EpB | Conversion | Selectivity |
|---|---|---|---|---|
| Temp | Press | Produced | of Butadiene | to EpB |
| 200 | 4.14 | 1.52 | 19.9 | 85.0 |
| 205 | 7.24 | 2.17 | 28.6 | 84.3 |
| 205 | 4.14 | 2.48 | 32.8 | 83.9 |
| 210 | 7.24 | 2.68 | 35.7 | 83.3 |

Example 2

Comparative Example 1 was repeated except that 100 ppm ammonia was added to the gaseous feed stream when the reactor pressure was increased to 4.14 bara after 20 hours of operation. At the conclusion of the 210 hours of operation, the catalyst was removed from the reactor and the amount of organic foulant was determined as described in Comparative Example 1. The percentage of organic foulant was determined to be 0.17% of the catalyst removed from the reactor. Catalyst performance at selected reaction conditions of temperature and pressure is summarized in Table III.

TABLE III

| Reaction Conditions | | Mole % EpB Produced | Conversion of Butadiene | Selectivity to EpB |
|---|---|---|---|---|
| Temp | Press | | | |
| 200 | 4.14 | 1.34 | 17.2 | 86.7 |
| 205 | 4.14 | 2.54 | 33.2 | 85.0 |
| 210 | 7.24 | 2.50 | 33.3 | 83.5 |

Example 3

Comparative Example 1 was repeated except that 250 ppm ammonia was added to the gaseous feedstream when the reactor pressure was increased to 4.14 bara after 20 hours of operation. At the conclusion of 210 hours of operation, the catalyst was removed from the reactor and the amount of organic foulant was determined in the as described in Comparative Example 1. The percentage of organic foulant was determined to be 0.50% of the catalyst removed from the reactor. Catalyst performance at selected reaction conditions of temperature and pressure is sumarized in Table IV.

TABLE IV

| Reaction Conditions | | Mole % EpB Produced | Conversion of Butadiene | Selectivity to EpB |
|---|---|---|---|---|
| Temp | Press | | | |
| 200 | 4.14 | 1.25 | 16.2 | 85.7 |
| 210 | 7.24 | 2.46 | 32.9 | 83.0 |

The results achieved in Comparative Example 1 and Examples 1–3 show that ppm levels of ammonia, a simple, gas phase chemical base, very effectively lowers the extent of catalyst fouling by organic residue. Levels as low as 50 ppm and as high as 250 ppm are essentially equally effective at preventing build-up of organic foulant in the reactor. Furthermore, catalytic activity and selectivity for EpB formation are not adversely affected by the addition of ppm levels of NH3 in the feedstream. The data in Tables I–IV establish that catalytic activities are substantially increased by the addition of these levels of ammonia to the reactor feedstream.

Example 4

Comparative Example 1 was repeated except that 15 ppm ammonia was added to the gaseous feed stream when the reactor pressure was increased to 4.14 bara after 20 hours of operation and the process was operated at 200° C. and 4.14 bara total pressure for a total of 167 hours. Catalytic activity at these conditions was 1.05 mole % EpB in the reactor effluent at a selectivity of 89.8% EpB, corresponding to 13.0% butadiene conversion. This result indicates that at levels as low as 15 ppmv, the presence of ammonia in the feed stream results in higher activity than when ammonia is not present in the feed. The presence of 15 ppmv ammonia in the reactor feed gives a 7% increase in catalytic activity as compared to catalyst activity when ammonia is not fed to the reactor.

Example 5

Comparative Example 1 was repeated except that the reactor pressure was maintained at approximately 1 bara (ambient pressure) for a total of 217 hours of operation. After 217 hours of operation, 100 ppmv of monomethylamine was added to the gaseous feed stream when the reactor pressure was increased to 4.14 bar. From this point forward, the process was operated using the same combinations of time, temperature and pressure as described in Comparative Example 1, i.e., 20 hours at 200° C. and 4.14 bara, 30 hours at 205° C. and 7.24 bara, 70 hours at 205° C. and 4.14 bara, and 70 hours at 205° C. and 7.24 bara. The steady state catalytic activity at 210° C. and 7.24 bara pressure was 2.77% mole % EpB at a selectivity of 82.8%, corresponding to 37.1% conversion of butadiene. The amount of organic foulant was determined according to the procedure described in Comparative Example 1. The percentage of organic foulant was determined to be 0.70% of the catalyst removed from the reactor.

The results obtained in Example 4 show that substituted amine compounds are very effective at lowering the extent of organic foulant produced during operation at high pressures and temperatures and do not adversely affect performance of the promoted, silver catalyst. In fact, comparison with the analogous data in Table I shows the catalytic activity is approximately 29% higher in the presence of 100 ppmv monomethylamine.

Comparative Example 2

Butadiene epoxidation was conducted in a pilot-scale, continuous epoxidation apparatus in which materials were recycled to the epoxidation reactor analogous to the production system depicted in the process flow diagram of U.S. Pat. No. 5,312,931. The epoxidation catalyst employed was similar to that in the previous examples, i.e., an alumina-supported silver catalyst containing 12 weight percent silver and 700 parts per million by weight cesium. The reactor was a 6.4 meter steel tube with an inside diameter of 4.1 cm. The reactor temperature was controlled by generating steam in a steel jacket with a diameter of 10 cm. A gas comprised of 60–70% butane, 9–10% butadiene, 18% oxygen, 1.5–2% water, 8–16% of argon/nitrogen/methane and 3–5 ppmv 2-chlorobutane was fed to the reactor at a rate of 175 standard liters/minute (SLM).

Maximum reactor temperature was maintained between 213–215° C. during the reaction period. Reaction pressure was 2.9 bara (42 psia) at the top of the reactor and 1.24 bara (18 psia) at the base of the down-flow reactor. On-line reaction analysis was conducted using in-line gas chromatographic analysis of a small slip stream (typically 100 cc/minute) of the 175 SLM overall flow through the reactor. Reaction analysis also was determined by separation and purification of EpB product. Thus, catalyst performance could be determined as kg of EpB produced per liter of catalyst volume over the course of the experiment. The process was operated for 114 days and produced 205 kilograms of EpB per liter of catalyst. During an 8 week period of operation, the average EpB production rate was 0.096 kg EpB per liter of catalyst-hour (6 pounds EpB per cubic foot of catalyst-hour).

Following the completion of this experiment, the catalyst, which was very difficult to remove from the tubular reactor due to buildup of organic foulant, was analyzed by ash analysis. Ash analysis was done to determine the amount of fouling occurring on the catalyst. Ash analysis data indicate the percentage of the initial sample remaining after high temperature calcination in a high temperature muffle furnace. Analysis revealed 93.1% sample retention following the ashing treatment, while ash analysis of a fresh sample of unused catalyst gave 99.9% residue. Thus, approximately 6.8% by weight of the sample was lost during calcination. This weight loss represents the amount of buildup of organic foulant on the surface of the catalyst during the course of the 114 day experiment.

Example 6

Comparative Example 2 was repeated except that 10–15 ppmv of ammonia was added to the gaseous feedstream and the experiment was continued for a period of 103 days to produce 269 kg EpB per liter of catalyst volume. For an 8-week period of operation, EpB production rate averaged 0.104 kg EpB per liter of catalyst-hour (6.5 pounds EpB per cubic foot of catalyst-hour). This represents an increase of over 8%, when NH3 was added at levels as low as 10–15 ppmv of the total flow to the reactor.

At the conclusion of the 103-day experiment, the catalyst was easily removed from the reactor. Ash analysis of the used catalyst gave 98.2% weight retention, indicating that organic foulant was approximately 1.7% of the catalyst weight. This is a substantially lower amount of foulant than that formed in Comparative Example 2 even though EpB produced per liter of catalyst was much higher (269 vs. 205 kg EpB) when 10–15 ppm ammonia was added to the feed stream.

The results in Comparative Example 2 and Example 6 demonstrate yet again that ppm levels of ammonia or amine in the gas phase feed composition greatly lowers the extent of organic foulant formation, thus greatly increasing useful catalyst life while not adversely affecting EpB formation. Furthermore, ease of catalyst removal is greatly facilitated when ammonia and/or amines are added to the feed stream composition.

Comparative Example 2 and Example 6 also illustrate the benefit of adding a base compound to the recovery process. The loss to diol was 11 g per kg of EpB obtained in Comparative Example 2 when aqueous potassium bicarbonate was added to the recovery process. The loss to diol was reduced to 1.4 g per kg of EpB produced in Example 6 when ammonia was present in the feed to the reactor. (The examples of U.S. Pat. No. 5,756,779 show that the loss to diol is about 50 g per kg EpB when no basic material is added to the recovery section of the process.) Thus, the addition of ammonia in the gaseous feed to the recovery process provides intimate mixing with the acidic components and greatly reduces hydrolysis of EpB to butanediols.

Comparative Example 3

Comparative Example 3 and Examples 7–10 were carried out in a reactor comprising a stainless steel, tubular reactor 45.7 cm (18 inches) long having an outside diameter of 6.35 mm (0.25 inches) and an inside diameter of 4.83 mm (0.19 inches). The reactor was jacketed with a brass collar 25.4 mm (1 inch) in diameter to maintain an approximate, isothermal catalyst temperature profile. An adjustable thermowell was inserted inside the catalyst bed. The catalyst (5.75 g) was loaded into the reactor and heated in flowing air in situ at 250° C. for 2 hours. The temperature was then lowered to 225° C. and the catalyst was "prechlorided" in a gas flow of 10 ppm 2-chlorobutane in n-butane for a period of 4 hours. The thermowell confirmed a nearly isothermal bed profile over the 30.5 cm (12 inches) length of the catalyst bed. The epoxidation of butadiene then was commenced by feeding to the reactor/catalyst a gaseous feed stream composed of 9% (mole) butadiene and 18% (mole) oxygen with the balance being n-butane diluent containing 2–3 ppm 2-chlorobutane at approximately 1 bara (15 psia) total pressure and a total flow rate of 310 cc (STP) per minute. The temperature of the catalyst bed was maintained as for a period of approximately 50 hours of total process time. Steady state was reached after approximately 20–25 hours of operation. Catalyst performance was monitored by means of an in-line gas chromatographic analysis using a gas sampling loop connected to a Hewlett-Packard 5890 Series Gas Chromatograph. Catalytic activity at steady state was 2.14 mole percent EPB at a selectivity of 92.2%.

Examples 7–10

The procedure described in Comparative Example 3 was repeated except that after approximately 20 hours of operation either ammonia, monomethylamine (MMA), dimethylamine (DMA), or diethylamine (DEA) was added to the gaseous feed stream with the oxygen, butadiene, and n-butane concentrations remaining constant. Each of these alkylamines was added at a concentration of 300 ppmv to the gaseous feed stream after 20 hours of on-line operation. Ammonia was added at incremental concentrations of 100, 300, and 500 ppmv. The epoxidation process utilizing the varying concentrations of ammonia or an alkylamine was operated for 20–40 hours to ensure that a new steady state catalytic activity had been attained for each nitrogenous base. After each steady state catalytic activity had been established, in all but one case the inclusion of ammonia or alkylamine in the gaseous feed stream was discontinued and another steady-state catalytic activity (with no ammonia or alkylamine present in the feed stream), which required approximately 20–40 hours of operation of the epoxidation process, was then established and measured. The catalytic activities of the steady state operations are shown in Table III wherein Conc means the concentration of ammonia or alkyl amine in the gaseous feed to the epoxidation process and MMA, DMA and DEA have the meanings set forth above.

TABLE V

| Ex. No. | NH$_3$/Amine Additive Compound | Conc | Mole % EpB Produced | Butadiene Conversion | Selectivity to EpB |
|---|---|---|---|---|---|
| 7 | None | 0 | 2.18 | 26.3 | 92.1 |
| 7 | NH$_3$ | 100 | 2.67 | 32.5 | 91.3 |
| 7 | NH$_3$ | 300 | 2.79 | 34.3 | 90.5 |
| 7 | NH$_3$ | 500 | 2.72 | 33.5 | 90.2 |
| 7† | None | 0 | 2.62 | 32.0 | 91.1 |
| 8 | None | 0 | 2.22 | 26.9 | 91.6 |
| 8† | MMA | 300 | 2.83 | 34.6 | 90.9 |
| 8 | None | 0 | 2.89 | 22.9 | 91.8 |
| 9 | DMA | 300 | 3.15 | 38.9 | 89.9 |
| 9† | None | 0 | 3.17 | 39.5 | 89.2 |
| 10 | None | 0 | 1.99 | 24.0 | 92.0 |
| 10 | DEA | 200 | 2.45 | 29.8 | 91.3 |

†Operation after ammonia or alkylamine had been fed.

The results reported in Table V show that the addition of ammonia and various amines with different levels of substitution and substituents at ppm levels from 100 to 500 ppmv concentration results in substantial increases in catalytic activity; e.g., increases in mole % EpB range between 23–66%, depending on the concentration or composition of the ammonia/amine added to the feedstream. Another benefit of including ammonia or an alkylamine in the feed to the epoxidation process is that catalytic activity following discontinuance of the ammonia/alkylamine feed remains approximately the same as when the ammonia/amine was added to the feedstream. The long term effect of ammonia/alkylamine addition or treatment suggests that the catalyst structure and/or composition has been changed during the period of addition.

Example 11

The procedure described in Comparative Example 3 was used to determine the long term effectiveness of ammonia to enhance the activity of a supported silver catalyst used to catalyze the selective monoepoxidation of butadiene to EpB. The activity of the catalyst before the inclusion of 300 ppmv ammonia in the gaseous feed stream to the epoxidation reactor was 2.0 mole percent EpB at a selectivity of 91.9%, corresponding to 24.2% butadiene conversion. Operation of the epoxidation process with 300 ppmv ammonia in the gaseous feed stream for 34.5 hours improved catalyst performance to 2.3 mole percent EpB at a selectivity of 91.9%. Operation of the process was continued in the absence of ammonia for 150 hours and catalyst activity was measured periodically. Catalyst activity as a function of time after discontinuance of the ammonia feed is shown in Table VI.

TABLE VI

| Hours of Operation After Discontinuance of Ammonia Feed | Mole % EpB Produced | Selectivity to EpB |
| --- | --- | --- |
| 0 | 2.30 | 91.9 |
| 10 | 2.30 | 91.0 |
| 20 | 2.30 | 91.0 |
| 40 | 2.26 | 91.2 |
| 60 | 2.28 | 91.0 |
| 100 | 2.23 | 91.3 |
| 125 | 2.21 | 91.2 |
| 150 | 2.24 | 91.1 |

The results reported in Table VI demonstrate that exposure to ammonia or an amine for sufficient periods of time results in long term increases in catalyst activity with no adverse affects on selectivity. Thus, ammonia and amines function as true catalyst promoters since, if desired, the ammonia or amine can be added only once or intermittently for short periods of time. However, if desired, ammonia and/or an amine can be added concurrently to the feedstream to give enhanced catalyst performance.

Comparative Example 4

Comparative Example 4 and Example 12 were carried out in a reactor comprising a stainless steel, tubular reactor 45.7 cm (18 inches) long having an outside diameter of 9.5 mm (0.375 inches) and an inside diameter of 7.75 mm (0.305 inches). The reactor was heated by means of a recirculating hot oil jacket around the tubular reactor. A catalyst sample weighing 12.0 grams of the same composition as used in previous examples was loaded into the reactor and heated in flowing air in situ at 250° C. for 2 hours. The temperature was then lowered to 180° C. and the catalyst was "prechlorided" in a gas flow of 10 ppm 2-chlorobutane in n-butane for a period of 30 minutes. A thermowell inserted into the full length of the catalyst bed confirmed a nearly isothermal bed profile over the 30.5 cm (12 inches) length of the catalyst bed. The reactor was heated by means of a recirculating hot oil jacket around the tubular reactor. The epoxidation of butadiene was commenced by feeding to the reactor/catalyst a gaseous feed stream composed of 9% butadiene and 18% oxygen, 10% argon, 63% n-butane (all molar concentrations) and 1 ppmv 2-chlorobutane at a total flow rate of 3.01 standard liters per minute (SLP). Reactor pressure was maintained at approximately 1.5 bara (22 psia) inlet pressure and 1.2 bara (17 psia) outlet pressure. Reaction temperature was maintained at 195° C. at the reactor inlet. Catalyst performance was monitored throughout the entire run by an in-line gas sampling loop that injected a gas sample from a slip stream of the reactor effluent into a Poraplot Q gas chromatographic column installed in an Hewlett-Packard 5890 Series Gas Chromatograph. After 14 days of operation, the catalyst was operating at 17.5% conversion of the butadiene fed and a selectivity to EpB of 93.5%. No ammonia/amine was added to the reactor feedstream over this period of operation.

Example 12

The procedure described in Comparative Example 4 was repeated except that 28 ppmv ammonia was included in the gaseous feed stream after the catalyst reached steady state activity. The performance of the catalyst over 14 days of operation is shown in Table VII wherein Time is the total days of operation, Temperature is the temperature (° C.) at the reactor inlet and Conversion is the mole percent conversion of butadiene. For the first 5 days, no ammonia was included in the gaseous feed to the reactor; for the next 7 days, 28 ppmv ammonia was included in the reactor feed; and no ammonia or amine was fed during days 13 and 14 of operation.

TABLE VII

| Time | Temp | Conversion | Selectivity |
| --- | --- | --- | --- |
| 5 | 195 | 18.0 | 93.5 |
| 12 | 195 | 20.6 | 94.3 |
| 13 | 195 | 23.1 | 93.0 |
| 14 | 191 | 18.0 | 93.5 |

The results obtained in Comparative Example 4 and Example 12 demonstrate that levels of ammonia as low as 28 ppmv in the reactor feed stream enhance catalytic activity, in this case by more than 14% relative to when ammonia is not present in the feed stream. The data in Table VII further illustrate that the increase in activity persists for long periods of time after ammonia is removed from the feed. More specifically, after ammonia removal, the reactor temperature could be lowered by 4° C. to 191° C. and still maintain catalyst performance equivalent to that before ammonia addition. These results confirm again the role of ammonia/amines as catalyst promoters; addenda that can be added once or during a short period of time to effect long term changes in catalyst performance.

The invention has been described in detail with particular reference to preferred embodiments thereof, but it will be understood that variations and modifications may be effected within the spirit and scope of the invention.

We claim:

1. Process for the preparation of the monoepoxide of an olefin reactant selected from norbornene, norbornadiene and olefins having the general formula

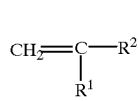

(I)

wherein $R^1$ is hydrogen or alkyl and $R^2$ is an aryl radical or the group

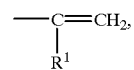

provided that the olefins of formula (I) contain more than 2 carbon atoms and do not contain any allylic hydrogen atoms, which comprises contacting a reaction gas comprising said olefin reactant, oxygen, an inert diluent, and at least 5 parts per million by volume (ppmv) of at least one nitrogen-containing basic compound with a supported silver epoxidation catalyst at a temperature of about 175 to 230° C.; and recovering a gas containing said monoepoxide of the olefin reactant.

2. Process according to claim 1 wherein the nitrogen-containing basic compound is ammonia or a mono-, di-, or tri-alkylamine having a boiling points of less than about 150° C.

3. Process according to claim 1 wherein the nitrogen-containing basic compound is ammonia or a mono- or di-alkylamine having a boiling point of less than about 150° C. containing up to about 12 carbon atoms and the epoxidation catalyst comprises a catalyst support material having deposited on its surface about 1 to 30 weight percent silver and about 10 to 5000 parts per million by weight (ppmw) of an epoxidation catalyst modifier selected from alkali earth metals, alkaline earth metals and thallium.

4. Process according to claim 3 wherein the reaction gas contains about 20 to 500 ppmv of the nitrogen-containing basic compound, the olefin reactant is 1,3-butadiene and the monoepoxide is 3,4-epoxy-1-butene.

5. A continuous process for the preparation of the monoepoxide of an olefin reactant selected from norbornene, norbornadiene and olefins having the general formula

(I)

wherein $R^1$ is hydrogen or alkyl and $R^2$ is an aryl radical or the group

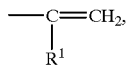

provided that the olefins of formula (I) contain more than 2 carbon atoms and do not contain any allylic hydrogen atoms, which comprises the steps of:

(1) continuously feeding a gas comprising about 3 to 30 mole percent of said olefin reactant, about 3 to 30 mole percent oxygen, about 40 to 90 mole percent of an inert diluent, and at least 5 parts per million by volume (ppmv) of at least one nitrogen-containing basic compound to an epoxidation zone containing a supported, silver epoxidation catalyst and maintained at a temperature of about 175 to 230° C.; and (2) continuously removing from the epoxidation zone a gas comprising about 0.5 to 5.0 mole percent of said monoepoxide of the olefin reactant, about 2 to 28 mole percent of said olefin reactant, about 2 to 28 mole percent oxygen and about 40 to 90 mole percent of said paraffin hydrocarbon.

6. Process according to claim 5 wherein the nitrogen-containing basic compound is ammonia or a mono-, di-, or tri-alkylamine having a boiling points of less than about 150° C.

7. Process according to claim 5 wherein the nitrogen-containing basic compound is ammonia or a mono- or di-alkylamine having a boiling point of less than about 150° C. containing up to about 12 carbon atoms and the epoxidation catalyst comprises a catalyst support material having deposited on its surface about 1 to 30 weight percent silver and about 10 to 5000 parts per million by weight (ppmw) of an epoxidation catalyst modifier selected from alkali earth metals, alkaline earth metals and thallium.

8. Process according to claim 7 wherein the reaction gas contains about 20 to 500 ppmv of the nitrogen-containing basic compound, the olefin reactant is 1,3-butadiene and the monoepoxide is 3,4-epoxy-1-butene.

9. A continuous process for the preparation of 3,4-epoxy-1-butene which comprises the steps of:

(1) continuously feeding a gas comprising about 3 to 30 mole percent of 1,3-butadiene, about 3 to 30 mole percent oxygen, about 40 to 90 mole percent of a paraffin hydrocarbon containing 1 to 6 carbon atoms wherein the oxygen:paraffin hydrocarbon mole ratio is in the range of about 0.03:1 to 0.75:1, about 20 to 500 parts per million by volume (ppmv) of at least one nitrogen-containing basic compound having a boiling point of less than about 150° C. to an epoxidation zone containing a supported, silver epoxidation catalyst and maintained at a temperature of about 185 to 225° C. and a pressure of about 1 to 10 bar absolute; and (2) continuously removing from the epoxidation zone a gas comprising about 0.5 to 5.0 mole percent of said monoepoxide of the olefin reactant, about 2 to 28 mole percent of said olefin reactant, about 2 to 28 mole percent oxygen and about 40 to 90 mole percent of said paraffin hydrocarbon.

10. Process according to claim 9 wherein the nitrogen-containing basic compound is ammonia or a mono-, di-, or tri-alkylamine containing up to about 12 carbon atoms and the epoxidation catalyst comprises a catalyst support material having deposited on its surface about 2 to 25 weight percent silver and about 20 to 3000 parts per million by weight (ppmw) of an epoxidation catalyst modifier selected from alkali earth metals, alkaline earth metals and thallium.

11. A continuous process for the preparation of 3,4-epoxy-1-butene which comprises the steps of:

(1) continuously feeding a gas comprising about 3 to 30 mole percent of 1,3-butadiene, about 3 to 30 mole percent oxygen, about 40 to 90 mole percent butane wherein the oxygen:butane mole ratio is in the range of about 0.03:1 to 0.75:1, and at least 5 parts per million by volume (ppmv) of ammonia to an epoxidation zone containing a supported, silver epoxidation catalyst comprising a catalyst support material having deposited on its surface about 2 to 25 weight percent silver and about 20 to 3000 parts per million by weight (ppmw) of an epoxidation catalyst modifier selected from cesium and rubidium and maintained at a temperature of about 175 to 230° C.; and (2) continuously removing from the epoxidation zone a gas comprising about 0.5 to 5.0 mole percent of said monoepoxide of the olefin reactant, about 2 to 28 mole percent of said olefin reactant, about 2 to 28 mole percent oxygen and about 40 to 90 mole percent butane.

12. Process according to claim 11 wherein the concentration of ammonia in the feed gas is about 20 to 500 ppmv.

13. A continuous process for the preparation of 3,4-epoxy-1-butene which comprises the steps of:

(1) continuously feeding a gas comprising about 3 to 30 mole percent of 1,3-butadiene, about 3 to 30 mole percent oxygen, about 40 to 90 mole percent methane wherein the oxygen:methane mole ratio is in the range of about 0.03:1 to 0.75:1, and at least 5 parts per million by volume (ppmv) of ammonia to an epoxidation zone containing a supported, silver epoxidation catalyst comprising a catalyst support material having deposited on its surface about 2 to 25 weight percent silver and about 20 to 3000 parts per million by weight (ppmw) of an epoxidation catalyst modifier selected from cesium and rubidium and maintained at a temperature of about 175 to 230° C.; and (3) continuously removing from the epoxidation zone a gas comprising about 0.5 to 5.0 mole percent of said monoepoxide of the olefin reactant, about 2 to 28 mole percent of said olefin reactant, about 2 to 28 mole percent oxygen and about 40 to 90 mole percent methane.

14. Process according to claim 11 wherein the concentration of ammonia in the feed gas is about 20 to 500 ppmv.

* * * * *